United States Patent
Anderson et al.

Patent Number: 5,817,114
Date of Patent: Oct. 6, 1998

[54] HYGIENIC TONGUE CLEANER

[76] Inventors: Lorrie E. Anderson, 1462 S. Colorado St., Apt. 1-H, Greenville, Miss. 38703; Portia E. Anderson, 2163 Florence-Byram Rd., Florence, Miss. 39073

[21] Appl. No.: 961,204

[22] Filed: Oct. 30, 1997

[51] Int. Cl.⁶ .................................................. A61B 17/24
[52] U.S. Cl. .......................................... 606/161; 606/131
[58] Field of Search ................... 606/131, 161; 15/160, 167.1, 143

[56] References Cited

U.S. PATENT DOCUMENTS

| | | | |
|---|---|---|---|
| D. 309,528 | 7/1990 | Valenti . | |
| D. 332,352 | 1/1993 | Caldwell et al. . | |
| 1,533,123 | 9/1925 | Lewis | 606/161 |
| 1,701,616 | 4/1929 | Gross | 606/161 |
| 1,891,864 | 12/1932 | Barrett . | |
| 2,218,072 | 10/1940 | Runnels | 606/161 |
| 2,491,274 | 12/1949 | McNiell . | |
| 3,943,592 | 3/1976 | Bheskar et al. . | |
| 5,613,262 | 3/1997 | Choy-Maldonado . | |

FOREIGN PATENT DOCUMENTS

| | | | |
|---|---|---|---|
| 2260905 | 5/1993 | United Kingdom | 606/131 |

*Primary Examiner*—Michael Powell Buiz
*Assistant Examiner*—Vy Quang Bui
*Attorney, Agent, or Firm*—Bacon & Thomas

[57] ABSTRACT

A hygienic tongue cleaner includes a support member having an upper surface area arranged so as to fit snugly within the roof area of a mouth of an individual user. The lower surface of the support member includes a tongue cleaner element or elements against which one's tongue may be rubbed to obtain a cleansing action of the upper surface of the tongue while the support member is retained in position within the roof area of the mouth. The support member may include teeth engaging portions that secure the support member against motion during the tongue rubbing and cleansing procedure. The location and arrangement of the tongue cleaner avoids generation of a gagging reflex in a user.

7 Claims, 1 Drawing Sheet

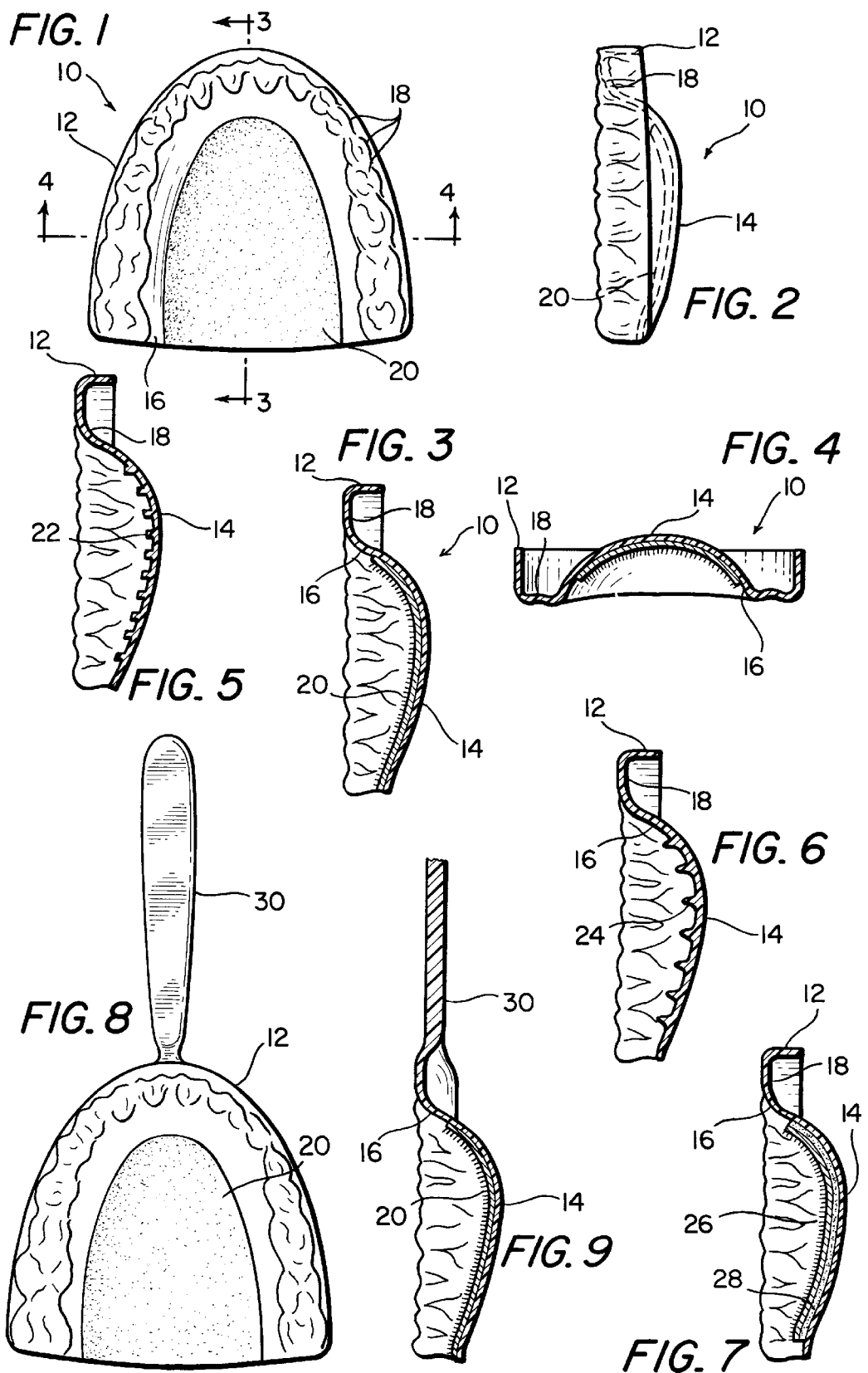

HYGIENIC TONGUE CLEANER

BACKGROUND OF THE INVENTION

1. Field of the Invention

This invention relates to hygienic tongue cleaning devices.

2. Related Art

It has been recognized in the field of oral hygiene that problems associated with odoriferous breath of individuals can be alleviated through diligent oral hygiene practices, including scraping the upper surface of one's tongue, particularly towards the rear of the tongue. Such scraping removes bacteria and other odor producing elements from the surface of the tongue without harmful effects to the tongue itself.

Numerous attempts have been made to provide tongue cleaning appliances for individual use, such cleaners, in their most elementary form, comprising a rigid, blade-like scraper element that can be grasped by an individual and pulled across the surface of one's tongue. Such scrapers include handles or manipulating portions that enable one to reach backwards towards the rear of the mouth to reach the rear upper surfaces of one's tongue.

In more advanced forms, tongue scrapers have been formed much like a toothbrush, that is, an end portion having bristles connected to a handle portion for manipulating the brush.

Still other forms of tongue scrapers include abrasive surfaces, rubber fingers, foam rubber elements and other similar cleaning devices having various shapes and forms intended to reach the upper rear surface portion of a tongue during a cleaning procedure.

In all instances, the use of such implements results in an involuntary gagging reaction in many users. The human oral cavity tends to instinctively react against foreign objects advancing towards the rear of the mouth toward the restricted throat area where the rear of the tongue normally rests. This involuntary gagging reflex prevents many people from using conventional tongue scrapers that must be inserted from the front of the mouth towards the rear while the implement is maneuvered to effect scraping of the upper surface of the tongue. Even extending the tongue to its maximum extent while using such implements does not eliminate the gagging reflex in many people, who cannot use such implements effectively due to this reaction.

BRIEF SUMMARY OF THE INVENTION

The present invention eliminates problems associated with the prior art by locating a hygienic tongue cleaning implement including a scraper surface or surfaces in the roof portion of one's mouth where it is retained much like an upper plate of teeth momentarily while the tongue is run across the cleaning element or elements in a natural setting. Moving the tongue forwardly and rearwardly across the cleaning elements effectively cleans the upper surface of the tongue, including the rearward surface, without inducing a gagging reflex because the cleaning action is occurring in a natural position within the roof portion of one's mouth.

The cleaner may be formed inexpensively from a single molded element for disposable, one-time use or multiple time uses, or may be made for long-time repeated use. The cleaner preferably includes one or more teeth receiving cavities or areas for temporarily anchoring the cleaner against forward and rearward movement during the cleaning procedure.

The tongue cleaning elements may be bristle, blade, abrasive or porous structures or any other material or element that will effectively produce a cleaning action when the upper surface of the tongue is rubbed across the material or element.

The cleaner may be used with or without an additional cleaning substance designed to enhance the cleaning action and to produce a refreshing taste sensation in one's mouth.

The tongue cleaner in accordance with the invention enables cleaning of the upper surface, including the rearward portion, of one's tongue without inducing a gagging reflex due to the natural action of the tongue against the cleaner within the roof area of one's mouth.

The invention is described in detail below in conjunction with the appended drawings.

BRIEF DESCRIPTION OF THE DRAWINGS

FIG. 1 is a bottom plan view of a hygienic tongue cleaner embodying the invention;

FIG. 2 is a side elevation view of the cleaner shown in FIG. 1;

FIG. 3 is a section view taken along line 3—3 of FIG. 1;

FIG. 4 is a section view taken along line 4—4 of FIG. 1; and

FIGS. 5–9 show alternate embodiments of the invention.

DETAILED DESCRIPTION OF PREFERRED EMBODIMENTS OF THE INVENTION

With reference to the appended drawings, a hygienic tongue cleaner 10 includes a support member 12 that has an upper surface 14 and a lower surface 16. A support member 12 in accordance with this embodiment comprising a thin molded or formed sheet of plastic or the like configured to closely fit within the roof portion of a human mouth.

The support portion 12 includes one or more recesses or areas 18 for receiving upper teeth of one's mouth when the cleaner is placed within the upper roof area of a mouth. In accordance with the illustrated embodiment of the invention, the recesses 18 are configured to receive a full upper set of teeth, much like an upper plate supporting artificial teeth. The support 12 may be custom fitted to an individual much like an upper plate of teeth, if desired.

The lower surface 16 has affixed thereto a tongue cleaner element 20 that may be constituted of a bristled or napped surface, or any other configuration that would effect scraping or brushing of a tongue when the upper surface of the tongue is rubbed against the element.

In use, the support member is installed in the roof area of one's mouth with the upper surface thereof against a mouth roof and the recesses 18 engaging upper teeth of the user so that the support member is restrained against forward and rearward movement when the tongue is pressed upwardly against the scraper element 20 and moved forwardly and backwardly against the cleaner element.

Paste, fluid, powder or other cleaning material may be utilized with the cleaner element, for example a toothpaste-like substance or other material that would enhance the cleaning action of the cleaning element and would include a flavoring or fragrance that would produce a refreshing, clean sensation in the mouth of the user.

Since the support member is placed in a natural position within the roof of the mouth of the user, motion of the tongue across the cleaner element would not induce a gagging reflex since there is no movement of a foreign object toward the back area of the mouth or throat of the user. Forward and rearward motion of the tongue relative to the cleaner element enables one to clean the upper surface of the tongue, including the rearward area thereof, without inducing a gagging reflex.

The support member and cleaner element may be produced by simple forming or molding techniques using inexpensive sheet plastic material for the support member and a napped or bristled material for the cleaner element. The device may be configured for one-time or multi-time use, and it could be formed of more substantial materials for repeated use and cleaning between uses. The support and cleaner elements could be provided to dentists in kit form to enable custom fitting to individual patients, if desired.

The cleaner element 20 could be formed of synthetic plastic or natural materials, including fabrics, provided that the cleaner element includes a surface or element that will effectively cleanse the surface of a tongue. Bristles, foam, abrasive pads, scraper blades and the like, or equivalents thereof, all are envisioned as usable for the tongue cleaner element.

For example, as illustrated in FIG. 5, the cleaner element may include scraper blades 22 extending from the lower surface of the support member 12, such blades 22 being attached to or extending from lower surface 16 of the member 12.

In another alternate embodiment, as shown in FIG. 6, the cleaner element of the invention may be formed as integral blades or scrapers 24 integrally formed with the support member 12 and extending downwardly from the lower surface 16.

In still another example of the invention, as shown in FIG. 7, a nap or bristle scraper element 26 may be connected to the lower surface 16 of the member 12 by a foam or soft backing material 28 that provides a cushion effect between the scraper 26 and the support member 12. The cushion material 28 could be used, of course, with any of the embodiments described or contemplated herein.

While the invention has been illustrated using recesses 18 for receiving multiple upper teeth, it is to be understood that the support member 12 could be formed so as to receive one or more upper teeth or could be formed in another manner so as to simply engage upper teeth or even the gum area of an individual who may have lost or had removed all or most of the upper teeth.

Thus, while the invention has been described in connection with a support member 12 having teeth engaging recesses, it is to be understood that such teeth engaging recesses may extend to gum receiving recesses as well, and furthermore the teeth engaging recesses may be constituted of a single tooth engaging recess that will effectively prevent forward and rearward movement of the tongue cleaner while the tongue is rubbed against the scraper element 20.

It is also contemplated that the support member 12 may be attached to or attachable to a handle means 30 as shown in FIGS. 8 and 9 to enable one to accurately locate the cleaner in one's mouth and to remove same after use.

It will be understood that the preferred embodiments of the invention described herein are exemplary only and that the invention may be constructed in various other forms that would be readily apparent to those skilled in the art without departing from the spirit and scope of the invention.

We claim:

1. A hygienic tongue cleaner comprising:

a support member having a lower surface and an upper surface convexly contoured to snugly fit within a mouth roof area; and a tongue cleaner element secured to and extending from the lower surface.

2. A hygienic tongue cleaner according to claim 1, said support member including a tooth engaging portion for engaging at least one upper tooth and for fixing the support member in position at a mouth roof location.

3. A hygienic tongue cleaner according to claim 2, wherein said support member is a one-piece molded member and said tooth engaging uppers portion comprises a tooth receiving cavity in said molded member.

4. A hygienic tongue cleaner according to claim 3, said upper tooth receiving cavity being formed to receive multiple upper teeth of an individual user of the cleaner.

5. A hygienic tongue cleaner according to claim 2, said cleaner element being selected from the group consisting of a napped material, bristles, an abrasive element, and a blade element.

6. A hygienic tongue cleaner according to claim 1, including a cushion element underlying the tongue cleaner element.

7. A hygienic tongue cleaner according to claim 1, said support member comprising a single piece molded member including a tooth engaging portion, said tooth engaging portion comprising a molded cavity for receiving a plurality of upper teeth; said tongue cleaner element comprising a plurality of cleaning devices extending downwardly from the lower surface of the support member.

* * * * *